United States Patent
Brackhagen et al.

(10) Patent No.: US 10,610,491 B2
(45) Date of Patent: Apr. 7, 2020

(54) COMPOSITION COMPRISING AN ORGANIC LIQUID DILUENT AND A SPECIFIC HYDROXYALKYL METHYLCELLULOSE

(71) Applicant: Dow Global Technologies LLC, Midland, MI (US)

(72) Inventors: Meinolf Brackhagen, Walsrode (DE); Matthias Knarr, Weser (DE); Roland Adden, Walsrode (DE)

(73) Assignee: DOW GLOBAL TECHNOLOGIES LLC

( * ) Notice: Subject to any disclaimer, the term of this patent is extended or adjusted under 35 U.S.C. 154(b) by 0 days.

(21) Appl. No.: 15/023,856

(22) PCT Filed: Sep. 15, 2014

(86) PCT No.: PCT/US2014/055574
§ 371 (c)(1),
(2) Date: Mar. 22, 2016

(87) PCT Pub. No.: WO2015/047763
PCT Pub. Date: Apr. 2, 2015

(65) Prior Publication Data
US 2016/0235682 A1    Aug. 18, 2016

Related U.S. Application Data
(60) Provisional application No. 61/882,040, filed on Sep. 25, 2013.

(51) Int. Cl.
| | |
|---|---|
| A61K 9/48 | (2006.01) |
| A61K 9/10 | (2006.01) |
| A61K 47/38 | (2006.01) |
| A61K 47/10 | (2017.01) |
| A61K 9/08 | (2006.01) |
| C08L 1/28 | (2006.01) |

(52) U.S. Cl.
CPC .............. *A61K 9/4866* (2013.01); *A61K 9/08* (2013.01); *A61K 9/10* (2013.01); *A61K 9/4808* (2013.01); *A61K 9/4816* (2013.01); *A61K 9/4891* (2013.01); *A61K 47/10* (2013.01); *A61K 47/38* (2013.01); *C08L 1/284* (2013.01)

(58) Field of Classification Search
None
See application file for complete search history.

(56) References Cited

U.S. PATENT DOCUMENTS

| | | |
|---|---|---|
| 3,493,407 A | 2/1970 | Greminger, Jr. et al. |
| 5,493,013 A | 2/1996 | Reichel |
| 6,235,893 B1 | 5/2001 | Reibert et al. |
| 6,891,034 B2 | 5/2005 | Dannhorn et al. |
| 9,408,915 B2 | 8/2016 | Wu et al. |

FOREIGN PATENT DOCUMENTS

| | | |
|---|---|---|
| CN | 102415998 | 4/2012 |
| CN | 102525876 | 3/2014 |
| EP | 0240773 A1 | 10/1987 |
| EP | 1847260 A2 | 10/2007 |
| EP | 1983004 A1 | 10/2008 |
| JP | H47-005116 B | 8/1972 |
| JP | J60-192702 | 10/1985 |
| WO | 2005115330 A2 | 12/2005 |
| WO | 2008047201 A2 | 4/2008 |
| WO | 2013154980 A1 | 10/2013 |
| WO | 2013154981 A1 | 10/2013 |
| WO | 2014014753 A1 | 1/2014 |

OTHER PUBLICATIONS

Frith (Transactions of the Faraday Society vol. 41, 1945).*
Van Den Mooter, The use of amorphous solid dispersions: A formulation strategy to overcome poor solubilitiy and dissolution rate, Drug Discovery Today, 2011.
Warren et al., Using polymeric precipitation inhibitors to improve the absorption of poorly water-soluble drugs: A mechanistic basis for utility, Journal of Drug Targeting, 2010,18 (10), pp. 704-731.
Raghavan et al., Crystallization of hydrocortisone acetate: influence of polymers, International Journal of Pharmaceutics, 2001, pp. 213-221, 212.
Lindberg et al., Distribution of substituents in O-Ethyl-O-(2-Hydroxyethyl) Cellulose, Carbohydrate Research, 1988, pp. 137-144, 176.
Bartelmus et al., Die Analytik von Celluloseathergruppen, Z. Anal. Chem., 1977, pp. 161-190, 286.
Friesen et al., Hydroxypropyl Methylcellulose Acetate Succinate-Based Spray-Dried Dispersions: An Overview, Molecular Pharmaceutics, 2008, pp. 1003-1019, vol. 5, No. 6.
Ghose et al., Atomic Physiochemical Parameters for Three-Dimensional-Structure-Directed Quantitative Structure-Activity Relationships, 2. Modeling Dispersive and Hydrophobis Interactions, Journal Chem. Inf. Comput. Sci., 1987, pp. 21-35, 27.

(Continued)

*Primary Examiner* — Patricia Duffy
*Assistant Examiner* — Garen Gotfredson

(57) ABSTRACT

A liquid composition which comprises an organic liquid diluent and a hydroxyalkyl methylcellulose which has a certain distribution of substituted hydroxyalkoxyl groups and unsubstituted hydroxyalkoxyl groups is stable over an extended time period. In the hydroxyalkyl methylcellulose hydroxyalkoxyl groups are classified into a fraction (A) and a fraction (B), wherein fraction (A) represents the sum of all molar fractions of substituted hydroxyalkoxyl groups having hydroxyl groups substituted further with methoxyl groups and fraction (B) represents the sum of all molar fractions of unsubstituted hydroxyalkoxyl groups having hydroxyl groups not substituted further with methoxyl groups and wherein the ratio fraction (A)/fraction (B) is at least 0.30. The liquid composition is useful for preparing a solid dispersion comprising at least one active ingredient in at least one hydroxypropyl methylcellulose by spray-drying.

20 Claims, No Drawings

(56) References Cited

OTHER PUBLICATIONS

Viswanadhan et al., Atomic Physiochemical Parameters for Three-Dimensional-Structure-Directed Quantitative Structure-Activity Relationships, 4. Additional Parameters for Hydrophobic and Dispersive Interactions and Their Application for an Automated Superposition of Certain Naturally Occurring Nucleoside Antibiotics, Journal Chem. Inf. Comput. Sci, 1989, pp. 163-172, 29.

Broto et al., Molecular structures: perception, autocorrelation descriptor and sar studies, Eur. J. Med. Chem.-Chim., 1984, pp. 71-78, 19, No. 1.

Ackman, Fundamental Groups in the Response of Flame Ionization Detectors to Oxygenated Aliphatic Hydrocarbons, J. of Gas Chromo., 1964, pp. 173-179, 2.

Addison et al., Flame Ionization Detector Molar Responses for Methyl Esters of Some Polyfunctional Metabolic Acids, J. of Gas Chromo., 1968, pp. 135-138, vol. 6.

Sweet et al., Quantitative Analysis by various G.L.C. Response-Factor Theories for partially Methylated and partially Ethylated Alditor Acetates, Carbohydrate Research, 1975, pp. 217-225, 40.

The Japanese Pharmacopoeia 14th Ed., Part I. Chapter 65: Viscosity Determination. pp. 104-7 (2001).

The Japanese Pharmacopoeia 14th Ed., Part II. Official Monographs. pp. 943-7 (2001).

The Japanese Pharmacopoeia 16th Ed., Chapter 2: 2.53 Viscosity Determination. pp. 67-8 (2011).

The Japanese Pharmacopoeia 16th Ed., Official Monographs: Hypromellose. pp. 940-2 (2011).

Al-Achi, A. et al., Integrated Pharmaceutics: Applied Performulation, Product Design, and Regulatory Science. Chapter 14: Capsule Product Design. pp. 320 & 323. Pharmaceutical Science. John Wiley & Sons, Inc., Hoboken, New Jersey (2013).

\* cited by examiner

COMPOSITION COMPRISING AN ORGANIC LIQUID DILUENT AND A SPECIFIC HYDROXYALKYL METHYLCELLULOSE

FIELD

This invention relates to a liquid composition comprising an organic liquid diluent and a specific hydroxyalkyl methylcellulose and to a solid dispersion comprising an active ingredient in a hydroxyalkyl methylcellulose.

INTRODUCTION

A large number of presently known drugs have a low solubility in water, and thus complex techniques are required to prepare a suitable dosage form. Much research is spent on the use of pharmaceutically acceptable water-soluble polymers in combination with drugs of low water solubility. The use of water-soluble polymers aims at reducing the crystallinity of the drug, thereby minimizing the activation energy necessary for the dissolution of the drug, as well as establishing hydrophilic conditions around the drug molecules, thereby improving the solubility of the drug itself to increase its bioavailability, i.e., its in vivo absorption by an individual upon administration. However, simple blending of a water-soluble polymer with a drug of low water solubility generally does not reduce the crystallinity of the drug nor generally improve said drug's solubility.

G. Van den Mooter, "The use of amorphous solid dispersions: A formulation strategy to overcome poor solubility and dissolution rate", *Drug Discov Today: Technol* (2011), doi:10.1016/j.ddtec.2011.10.002, discusses the preparation of amorphous solid dispersions to increase the bioavailability of poorly soluble drugs by improving their rate and extent of dissolution. A commonly applied manufacturing method for preparing amorphous solid dispersions is spray-drying. The spray-drying process starts from a solution of the drug and a carrier in a common organic solvent or a mixture of aqueous and organic solvents. This solution is atomized using a nozzle and the solvent is subsequently quickly evaporated (order of magnitude is milliseconds). The very fast solvent evaporation contributes to the amorphous state of the solid dispersion.

Dallas B. Warren et al. (*Journal of Drug Targeting*, 2010; 18(10): 704-731) have studied the use of water-soluble cellulose ethers as polymeric precipitation inhibitors, such as carboxymethyl cellulose (CMC), methyl cellulose (MC), hydroxyethyl cellulose (HEC), and hydroxypropylmethyl cellulose (HPMC) to improve the absorption of poorly water-soluble drugs.

S. L. Raghavan et al. (International Journal of Pharmaceutics 212 (2001) 213-221), have studied the influence of HPMC, MC, polyvinyl pyrrolidone (PVP) and polyethylene glycol (PEG400) on the crystallization of hydrocortisone acetate (HA).

International Patent Application WO2008/047201 discloses solid dispersions which comprise a poorly water soluble ionizable drug, a cationic species, and a dispersion polymer, such as hydroxypropyl methylcellulose (HPMC). According to the examples a drug and HPMC (E3 Prem LV; Methocel®, available from The Dow Chemical Company, Midland, Mich.) are mixed with water and methanol to form spray solutions. Solid spray-dried dispersions of the drug in HPMC are produced from this solution.

Unfortunately, compositions comprising an organic liquid diluent and a cellulose ether, such as hydroxypropyl methylcellulose, often are not storage stable but exhibit a huge viscosity increase after storage of the liquid composition over an extended time period. The viscosity increase can often be avoided by storing the liquid composition below room temperature, but this is often undesirable since it complicates storage and adds to storage costs. Moreover, the observed viscosity increase often limits the achievable content of the cellulose ether in the liquid composition, thus adding transportation and solvent recovery costs.

In view of the high importance and large number of poorly water soluble drugs, it is an object of the present invention to provide new liquid compositions which comprise an organic liquid diluent and a cellulose ether into which active ingredients can be incorporated, such as poorly water-soluble drugs, and which can be spray-dried to produce solid dispersions comprising the active ingredient in a cellulose ether. A preferred object of the present invention is to provide new liquid compositions comprising an organic liquid diluent and a cellulose ether which have a better viscosity stability upon storage than known comparable liquid compositions comprising an organic liquid diluent and at a cellulose ether.

SUMMARY

Surprisingly, it has been found that the viscosity stability upon storage of liquid compositions comprising an organic liquid diluent and a hydroxyalkyl methylcellulose can be improved, i.e., the rate of viscosity increase can be reduced, if a hydroxyalkyl methylcellulose of a specific ratio of substituted and unsubstituted hydroxyalkoxyl groups is incorporated into the liquid composition.

Accordingly, one aspect of the present invention is a liquid composition which comprises an organic liquid diluent and at least one hydroxyalkyl methylcellulose wherein hydroxyalkoxyl groups are classified into a fraction (A) and a fraction (B), wherein fraction (A) represents the sum of all molar fractions of substituted hydroxyalkoxyl groups having hydroxyl groups substituted further with methoxyl groups and fraction (B) represents the sum of all molar fractions of unsubstituted hydroxyalkoxyl groups having hydroxyl groups not substituted further with methoxyl groups and wherein the ratio fraction (A)/fraction (B) is at least 0.30.

Another aspect of the present invention is the use of the liquid composition as defined above that additionally comprises at least one active ingredient, for preparing a solid dispersion comprising at least one active ingredient in at least one hydroxyalkyl methylcellulose.

Yet another aspect of the present invention is a solid dispersion which comprises at least one active ingredient in at least one hydroxyalkyl methylcellulose wherein the ratio fraction (A)/fraction (B) is at least 0.30, as defined above.

Yet another aspect of the present invention is a process for producing the solid dispersion as defined further above which comprises the steps of providing the liquid composition as defined above, which additionally comprises at least one active ingredient, and removing liquid diluent from the liquid composition.

Yet another aspect of the present invention is a process for coating a dosage form which comprises the step of contacting the liquid composition as defined above with the dosage form.

Yet another aspect of the present invention is a process for the manufacture of capsules which comprises the step of contacting the liquid composition as defined above with dipping pins.

DETAILED DESCRIPTION

In the hydroxyalkyl methylcellulose utilized in the present invention hydroxyalkoxyl groups are classified into a fraction (A) and a fraction (B). Fraction (A) represents the sum of all molar fractions of substituted hydroxyalkoxyl groups, i.e., hydroxyalkoxyl groups having hydroxyl groups (of the hydroxyalkoxyl groups) substituted further with methoxyl groups. Fraction (B) represents the sum of all molar fractions of unsubstituted hydroxyalkoxyl groups, i.e., hydroxyalkoxyl groups having hydroxyl groups (of the hydroxyalkoxyl groups) not substituted further with methoxyl groups.

The ratio fraction (A)/fraction (B) is at least 0.30, preferably at least 0.35, more preferably at least 0.40, even more preferably at least 0.45, most preferably at least 0.50, and particularly at least 0.53. Typically the ratio fraction (A)/fraction (B) is up to 0.90, more typically up to 0.80, even more typically up to 0.70 or 0.65, and most typically up to 0.60. The determination of the distribution of ether substituents, such as methoxyl and hydroxyalkoxyl groups, in cellulose ethers, such as hydroxyalkyl methylcellulose, is generally known and e.g., described in Carbohydrate Research, 176 (1988) 137-144, Elsevier Science Publishers B.V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg. The determination of the ratio fraction (A)/fraction (B) is described in detail in the Examples section.

The hydroxyalkyl methylcellulose has a cellulose backbone having β-1,4 glycosidically bound D-glucopyranose repeating units, designated as anhydroglucose units in the context of this invention. Preferred hydroxyalkyl methylcelluloses are hydroxyethyl methylcelluloses, hydroxybutyl methylcelluloses, and more preferably hydroxypropyl methylcelluloses. Preferred are hydroxyalkyl methylcelluloses and most preferred are hydroxypropyl methylcelluloses, which have an MS(hydroxyalkoxyl) and a DS(methoxyl) described below. MS(hydroxyalkoxyl) and a DS(methoxyl) are abbreviated as MS and DS. The MS(hydroxyalkoxyl) is the average number of moles of hydroxyalkoxyl groups per anhydroglucose unit in the hydroxyalkyl alkylcellulose. It is to be understood that during the hydroxyalkylation reaction the hydroxyl group of a hydroxyalkoxyl group bound to the cellulose backbone can be further etherified by a methylation agent, and/or a hydroxyalkylation agent. Multiple subsequent hydroxyalkylation etherification reactions with respect to the same carbon atom position of an anhydroglucose unit yields a side chain, wherein multiple hydroxyalkoxyl groups are covalently bound to each other by ether bonds, each side chain as a whole forming a hydroxyalkoxyl substituent to the cellulose backbone. The term "hydroxyalkoxyl groups" thus has to be interpreted in the context of the MS(hydroxyalkoxyl) and the ratio fraction (A)/fraction (B) as referring to the hydroxyalkoxyl groups as the constituting units of hydroxyalkoxyl substituents, which either comprise a single hydroxyalkoxyl group or a side chain as outlined above, wherein two or more hydroxyalkoxy units are covalently bound to each other by ether bonding. Within this definition it is not important whether the terminal hydroxyl group of a hydroxyalkoxyl substituent is further alkylated, e.g. methylated, or not; both alkylated and non-alkylated hydroxyalkoxyl substituents are included for the determination of MS(hydroxyalkoxyl). The hydroxyalkyl methylcellulose generally has a molar substitution of hydroxyalkoxyl groups in the range of 0.05 to 1.00, preferably 0.08 to 0.90, more preferably 0.12 to 0.60, most preferably 0.15 to 0.50, and particularly 0.21 to 0.35.

The average number of hydroxyl groups substituted by methoxyl groups per anhydroglucose unit is designated as the degree of substitution of methoxyl groups, DS(methoxyl). In the above-given definition of DS, the term "hydroxyl groups substituted by methoxyl groups" is to be construed within the present invention to include not only methylated hydroxyl groups directly bound to the carbon atoms of the cellulose backbone, but also methylated hydroxyl groups of hydroxyalkoxyl substituents bound to the cellulose backbone. The hydroxyalkyl methylcelluloses preferably have a DS(methoxyl) in the range of 1.4 to 2.5, more preferably 1.6 to 2.4, even more preferably 1.7 to 2.2, most preferably from 1.8 to 2.1, and particularly from 1.9 to 2.05.

The degree of substitution of methoxyl groups (DS) and the molar substitution of hydroxyalkoxyl groups (MS) can be determined by Zeisel cleavage of the hydroxyalkyl methylcellulose with hydrogen iodide and subsequent quantitative gas chromatographic analysis (G. Bartelmus and R. Ketterer, Z. Anal. Chem., 286 (1977) 161-190). When the hydroxyalkyl methylcellulose is hydroxypropyl methylcellulose (HPMC), the determination of the % methoxyl and % hydroxypropoxyl is carried out according to the United States Pharmacopeia (USP 35, "Hypromellose", pages 3467-3469). The procedure is described in more details in the Examples. The values obtained are % methoxyl and % hydroxypropoxyl. These are subsequently converted into degree of substitution (DS) for methoxyl substituents and molar substitution (MS) for hydroxypropoxyl substituents. Residual amounts of salt are taken into account in the conversion.

The hydroxyalkyl methylcellulose incorporated in the liquid composition and the solid dispersion of the present invention generally has a viscosity of from 1.2 to 100 mPa·s, preferably from 1.2 to 50 mPa·s, more preferably from 1.8 to 10 mPa·s, most preferably from 2.4 to 7 mPa·s, and in particular from 3.0 to 5.0 mPa·s, measured as a 2 wt.-% solution in water at 20° C. The 2% by solution of hydroxyalkyl methylcellulose in water is prepared according to United States Pharmacopeia (USP 35, "Hypromellose", pages 3467-3469), followed by an Ubbelohde viscosity measurement according to DIN 51562-1:1999-01 (January 1999).

Methods of making the hydroxyalkyl methylcelluloses utilized in the present invention are described in detail in the Examples. Some aspects of the process for making the above-described hydroxyalkyl methylcelluloses wherein the ratio fraction (A)/fraction (B) is at least 0.30, preferably at least 0.35, more preferably at least 0.40, even more preferably at least 0.45, most preferably at least 0.50, and particularly at least 0.53 are described in more general terms below.

Processes for preparing the above-described hydroxyalkyl methylcelluloses having a ratio fraction (A)/fraction (B) of at least 0.30 are known in the art and described, e.g., in U.S. Pat. No. 5,493,013 and in Japanese Patent Application No. J60-192702.

Generally speaking, the process for preparing a hydroxyalkyl methylcellulose with an above-described ratio fraction (A)/fraction (B) comprises the steps of i) preparing alkali cellulose, ii) carrying out a hydroxyalkylation reaction by reacting the alkali cellulose with a hydroxyalkyl etherifying agent, preferably at a temperature from 50 to 95° C., more preferably 60 to 80° C., preferably for 20 to 200 min., more preferably for 30 to 90 min., and iii) subsequently adding a methyl etherifying agent to carry out a methylation reaction after the hydroxyalkylation reaction. A minor amount of the methyl etherifying agent may already be present in step ii) of the process, but it is typically only present in an amount of 0 to 20 percent, more typically 0 to 10 percent, and most typically 0 to 5 percent, based on the total weight of the methyl etherifying agent in steps ii) and iii). In any case, the amount of methyl etherifying agent present during step ii) (in moles per mole anhydroglucose units in the cellulose) should generally not exceed the amount of alkalizing agent present during step ii) in order to allow for a sufficient hydroxyalkylation reaction. Step iii) is preferably conducted in the presence of a second amount of an alkalizing agent. The addition of the second amount of the alkalizing agent in step iii) is preferably conducted at a temperature of 30 to 95° C., preferably 30 to 60° C., before the reaction is continued at a temperature of 60 to 95° C., preferably 75 to 85° C.

The alkalizing agent utilized in step i) and preferably in step iii) is preferably an aqueous solution of sodium hydroxide, most preferably a 45-50 weight percent aqueous sodium hydroxide solution. Typically from 1.0 to 5.0, more typically from 2.0 to 4.0 and most typically from 2.5 to 3.5 molar equivalents of alkalizing agent per mole of anhydroglucose units in the cellulose are utilized in step i). Typically from 0.2 to 5.0, more typically from 0.5 to 2.0 and most typically from 0.65 to 0.85 molar equivalents of hydroxyalkyl etherifying agent per mole of anhydroglucose units in the cellulose are utilized in step ii). Typically from 1.0 to 10, more typically from 3.0 to 8.0 and most typically 5.0 to 6.5 molar equivalents of methyl etherifying agent and typically from 1.0 to 5.0, more typically from 2.0 to 3.0 and most typically from 2.1 to 2.4 molar equivalents of alkalizing agent per mole of anhydroglucose units in the cellulose are utilized in step iii).

The hydroxyalkyl etherifying agent in step ii) preferably is ethylene oxide or butylene oxide or, more preferably, propylene oxide. A preferred methyl etherifying agent for carrying out the methylation reaction in step iii) is a methyl halide, more preferably methyl chloride.

By controlling the adding order of the hydroxyalkyl etherifying agent and the methyl etherifying agent, the substitution with methoxyl groups will be subsequent to the formation of a major portion of hydroxyalkoxyl groups.

One way of producing hydroxyalkyl methylcelluloses having a ratio fraction (A)/fraction (B) of at least 0.30 is described in detail in Japanese Patent Application No. J60-192702, published as unexamined application on Oct. 1, 1985 and having the filing date of Mar. 14, 1984 and the filing number 59-48389. Hydroxyalkyl methylcelluloses having a ratio fraction (A)/fraction (B) of at least 0.30 are preferably produced as described in Examples 1-3 of this Japanese Patent Application, except that the molar equivalents of hydroxyalkyl etherifying agent and methyl etherifying agent per mole of anhydroglucose units in the cellulose are adapted to achieve the desired MS(hydroxyalkoxyl) and DS(methoxyl). According to the process disclosed in this Japanese Patent Application, alkali cellulose is reacted with an alkylene oxide and a methyl halide in such a manner that as a first step, alkylene oxide is caused to react with the alkali cellulose containing an alkali in an amount corresponding to 5-80 mol %, preferably 10-70 mol %, of the total methyl halide quantity to be consumed in the reaction, in the absence or presence of an alkyl halide, and thereafter, as a second step, an alkali hydroxide and an alkyl halide are added and a reaction caused. In the first step the reaction temperature is preferably 30-90° C. and the reaction time is ideally 0.5-5 hours. According to the preferred embodiment and according to Examples 1-3, in the first step alkylene oxide is caused to react with the alkali cellulose in the absence of the alkyl halide.

The composition of the present invention is liquid at 25° C. and atmospheric pressure and comprises an organic liquid diluent, in addition to at least one hydroxyalkyl methylcellulose as described above. The term "organic liquid diluent" as used herein means an organic solvent or a mixture of two or more organic solvents that is liquid at 25° C. and atmospheric pressure. Preferred organic liquid diluents are polar organic solvents having one or more heteroatoms, such as oxygen, nitrogen or halogen like chlorine. More preferred organic liquid diluents are alcohols, for example multifunctional alcohols, such as glycerol, or preferably monofunctional alcohols, such as methanol, ethanol, isopropanol or n-propanol; ethers, such as tetrahydrofuran, ketones, such as acetone, methyl ethyl ketone, or methyl isobutyl ketone; acetates, such as ethyl acetate; halogenated hydrocarbons, such as methylene chloride; or nitriles, such as acetonitrile. More preferably the organic liquid diluents have 1 to 6, most preferably 1 to 4 carbon atoms. The liquid composition of the present invention may additionally comprise water; however, the liquid composition should comprise more than 50, more preferably at least 65, and most preferably at least 75 weight percent of an organic liquid diluent and less than 50, more preferably up to 35, and most preferably up to 25 weight percent of water, based on the total weight of the organic liquid diluent and water. Specific examples of preferred organic liquid diluents, optionally mixed with minor amounts of water are: methanol, tetrahydrofuran, methylene chloride, a blend of 80 to 95 weight percent of methanol and 20 to 5 weight percent of water, a blend of 80 to 95 weight percent of tetrahydrofuran and 20 to 5 weight percent of water, a blend of 55 to 85 weight percent of acetone and 45 to 15 weight percent of water, a blend of 15 to 85 weight percent of acetone and 85 to 15 weight percent of methanol, a blend of 15 to 85 weight percent of methyl ethyl ketone and 85 to 15 weight percent of methanol, a blend of 30 to 50 weight percent of acrylonitrile and 70 to 50 weight percent of a $C_{1-4}$-monoalcohol, such as methanol, ethanol, isopropylalcohol, or n-propanol; a blend of 30 to 50 weight percent of methanol and 70 to 50 weight percent of tetrahydrofuran or ethyl acetate, or a blend of 70 to 90 weight percent of ethanol and 10 to 30 weight percent of tetrahydrofuran or ethyl acetate.

The liquid composition of the present invention comprising an organic liquid diluent and an above-described hydroxyalkyl methylcellulose has been found to have a surprisingly stable viscosity upon storage. Surprisingly, it has been found that the liquid composition of the present invention has a better viscosity stability, i.e., it exhibits a smaller rate of viscosity increase after storage of the liquid composition over an extended time period than a comparable liquid composition which comprises a hydroxyalkyl methylcellulose having a ratio fraction (A)/fraction (B) of less than 0.30.

When the liquid composition of the present invention comprises an organic liquid diluent and 10 weight percent of the above-described hydroxyalkyl methylcellulose, based on the total weight of the liquid composition, its viscosity at 25° C. 60 minutes after its preparation typically is in the range of 20 to 5000 mPa·s, more typically 50 to 2000 mPa·s, most typically 100 to 1000 mPa·s, and particularly 150 to 500 mPa·s, measured as described in the Example section. When such liquid composition of the present invention, is stored for 18 hours or more at 25° C., typically the viscosity of the liquid composition is not more than the 10-fold viscosity, more typically not more than the 5-fold viscosity, and most typically not more than the 2.5-fold viscosity of the liquid composition at 25° C. that is measured 60 minutes after the liquid composition has been prepared. Accordingly, the liquid composition of the present invention comprising an organic liquid diluent and an above-described hydroxyalkyl methylcellulose does not tend to undergo undesired viscosity increase upon storage at room temperature. The reduced tendency to viscosity increase allows a higher concentration of at least one above-described hydroxyalkyl methylcellulose in a liquid composition comprising an organic liquid diluent while still preserving the flowability of the liquid composition. The increased viscosity stability upon storage, hereafter "storage stability", is of particular importance if the composition of the present invention is directly used in liquid form, for example in the form of a suspension, a sprayable composition, or a syrup as described further below. However, the increased storage stability is also of high importance if the liquid diluent is removed from the liquid composition to produce various dosage forms as described further below. The increased storage stability increases the processing window, i.e., the possible time period from the preparation of the liquid composition until its further processing.

The liquid composition of the present invention is useful as an excipient system for active ingredients and particularly useful as an intermediate for preparing an excipient system for active ingredients, such as fertilizers, herbicides or pesticides, or biologically active ingredients, such as vitamins, herbals and mineral supplements and drugs. Accordingly, the liquid composition of the present invention preferably comprises one or more active ingredients, most preferably one or more drugs. The term "drug" is conventional, denoting a compound having beneficial prophylactic and/or therapeutic properties when administered to an animal, especially humans. Preferably, the drug is a "low-solubility drug", meaning that the drug has an aqueous solubility at physiologically relevant pH (e.g., pH 1-8) of about 0.5 mg/mL or less. The invention finds greater utility as the aqueous solubility of the drug decreases. Thus, liquid compositions and the solid dispersions of the present invention are preferred for low-solubility drugs having an aqueous solubility of less than 0.1 mg/mL or less than 0.05 mg/mL or less than 0.02 mg/mL, or even less than 0.01 mg/mL where the aqueous solubility (mg/mL) is the minimum value observed in any physiologically relevant aqueous solution (e.g., those with pH values between 1 and 8) including USP simulated gastric and intestinal buffers.

The hydroxyalkyl methylcellulose comprised in the liquid composition and in the solid dispersion of the present invention is able to maintain the concentration of poorly water-soluble active ingredients, such as poorly water-soluble drugs in aqueous solutions at supersaturation levels. A considerably higher concentration of a poorly water-soluble active ingredient in an aqueous solution can be maintained than in the absence of a hydroxyalkyl methylcellulose. The degree of supersaturation of a poorly water-soluble active ingredient in an aqueous solution depends on various factors, such as the physical stability and the dissolution rate of a given active ingredient. Dwayne T. Friesen et al. in MOLECULAR PHARMACEUTICS VOL. 5, NO. 6, 1003-1019, 2008 have classified compounds with a structurally diverse range of physicochemical properties on a physical property map Tm/Tg ratio versus log P. The log P value is a standard measure of the lipophilicity of a compound. Log P, defined as the base 10 logarithm of the ratio of (1) the drug concentration in an octanol phase to (2) the drug concentration in a water phase when the two phases are in equilibrium with each other, is a widely accepted measure of hydrophobicity. Log P may be measured experimentally or calculated using methods known in the art. When using a calculated value for Log P, the highest value calculated using any generally accepted method for calculating Log P is used. Calculated Log P values are often referred to by the calculation method, such as C log P, A log P, and M log P. The Log P may also be estimated using fragmentation methods, such as Crippen's fragmentation method (27 J. Chem. Inf. Comput. Sci. 2 1 (1987)); Viswanadhan's fragmentation method (29 J. Chem. Inf. Comput. Sci. 163 (1989)); or Broto's fragmentation method (19 Eur. J. Med. Chem.-Chim. Theor. 7 1 (1984)).

$$\log P_{oct/wat} = \log\left(\frac{[\text{solute}]_{octanol}}{[\text{solute}]_{water}^{un\text{-}ionized}}\right)$$

Compounds with high log P values are very hydrophobic and tend to have extremely low water solubilities (often less than 1 µg/mL when their melting points are above about 100° C.) and low propensities for wetting when placed into water.

Tm is the melting temperature and Tg is the glass transition temperature of the compound at atmospheric pressure. Dwayne T. Friesen et al. have divided the compounds into four groups based on their position on this physical property map Tm/Tg ratio versus log P (FIG. 14 on page 1018 in MOLECULAR PHARMACEUTICS VOL. 5, NO. 6, 2008). The first group, Group 1, consists of compounds with relatively low Tm/Tg ratios (<1.25 K/K) and low to moderate log P values (less than about 6); Compounds in Group 2 have somewhat higher Tm/Tg ratios (1.25-1.4) and low to moderate log P values (less than about 6). Compounds in Group 3 have even higher Tm/Tg values (greater than 1.4) and low to moderate log P values (less than about 6). Finally, Group 4 compounds have high log P values (at least about 6).

A preferred aspect of the present invention is a liquid composition or a solid dispersion which comprises at least one hydroxyalkyl methylcellulose as described above and additionally at least one active ingredient that has a Tm/Tg ratio of more than 1.0 up to 1.8, preferably more than 1.1 up to 1.6, more preferably from 1.15 to 1.5, most preferably from 1.25 to 1.40, wherein the melting temperature Tm and the glass transition temperature Tg each are in Kelvin. The active ingredient preferably has a log P of more than 1 up to 11, preferably 1.5 to 8, most preferably 2 to 6.

The active ingredient does not need to be a low-solubility active ingredient in order to benefit from this invention, although low-solubility active ingredients represent a preferred class for use with the invention. An active ingredient that exhibits appreciable aqueous solubility in the desired environment of use may have an aqueous solubility up to 1 to 2 mg/mL, or even as high as 20 to 40 mg/mL. Useful low-solubility drugs are listed in the International Patent Application WO 2005/115330, pages 17-22.

The liquid composition of the present invention preferably comprises from 1 to 40, more preferably from 2.5 to 30, most preferably from 5 to 20, and particularly from 7 to 15 weight percent of at least one hydroxyalkyl methylcellulose as described above; preferably from 40 to 99, more preferably from 54.9 to 97.4, most preferably from 65 to 94.5 and particularly from 70 to 92 weight percent of i) an organic liquid diluent or ii) an organic liquid diluent blended with a minor amount of water, e.g. an amount of water described further above; and preferably from 0 to 40, more preferably from 0.1 to 40, most preferably from 0.5 to 25, and particularly from 1 to 15 weight percent of an active ingredient, based on the total weight of the liquid composition.

In one aspect of the invention the liquid composition of the present invention comprising at least one hydroxyalkyl methylcellulose as described above, one or more active ingredients and optionally one or more adjuvants can be used in liquid form, for example in the form of a suspension, a sprayable composition, or a syrup. The liquid composition is useful, e.g., for oral, ocular, topical, rectal or nasal applications. The liquid diluent should generally be pharmaceutically acceptable, such as ethanol or glycerol, optionally mixed with minor amounts of water as described above.

In another aspect of the invention the liquid composition of the present invention is used for producing a solid dispersion comprising at least one active ingredient, such as a drug described further above, in at least one hydroxyalkyl methylcellulose as described above and optionally one or more adjuvants. The solid dispersion is produced by removing the liquid diluent from the composition. The liquid diluent is the liquid organic diluent, optionally blended with a minor amount of water as described above; i.e., when the composition comprises water as an optional additive, organic liquid diluent and water are removed from the liquid composition to prepare the solid dispersion of the present invention.

One method of removing the liquid diluent from the liquid composition is by casting the liquid composition into a film or a capsule or by applying the liquid composition onto a solid carrier that in turn may comprise an active ingredient. A preferred method of producing the solid dispersion is by spray-drying. The term "spray-drying" refers to processes involving breaking up liquid mixtures into small droplets (atomization) and rapidly removing solvent from the mixture in a spray-drying apparatus where there is a strong driving force for evaporation of solvent from the droplets. Spray-drying processes and spray-drying equipment are described generally in Perry's Chemical Engineers' Handbook, pages 20-54 to 20-57 (Sixth Edition 1984). More details on spray-drying processes and equipment are reviewed by Marshall, "Atomization and Spray-Drying," 50 Chem. Eng. Prog. Monogr. Series 2 (1954), and Masters, Spray Drying Handbook (Fourth Edition 1985). A useful spray-drying process is described in the International Patent Application WO 2005/115330, page 34, line 7-page 35, line 25.

The solid dispersion of the present invention preferably comprises from 20 to 99.9 percent, more preferably from 30 to 98 percent, and most preferably from 60 to 95 percent of a hydroxyalkyl methylcellulose a) as described above, and preferably from 0.1 to 80 percent, more preferably from 2 to 70 percent, and most preferably from 5 to 40 percent of an active ingredient b) as described above, based on the total weight of the hydroxyalkyl methylcellulose a) and the active ingredient b). The combined amount of the hydroxyalkyl methylcellulose a) and the active ingredient b) is preferably at least 70 percent, more preferably at least 80 percent, and most preferably at least 90 percent, based on the total weight of the solid dispersion. The remaining amount, if any, are one or more of the adjuvants c) as described below. The solid dispersion can comprise one or more of the hydroxyalkyl methylcelluloses a), one or more of the active ingredients b), and optionally one or more of the adjuvants c), however their total amount is generally within the above-mentioned ranges.

Once the solid dispersion comprising at least one active ingredient in at least one hydroxyalkyl methylcellulose has been formed, several processing operations can be used to facilitate incorporation of the dispersion into a dosage form. These processing operations include drying, granulation, and milling. The inclusion of optional adjuvants in the solid dispersion may be useful in order to formulate the composition into dosage forms, such as tablets, pills, granules, pellets, caplets, microparticles, fillings of capsules, or into pastes, creams, suspensions or slurries. The amount of the active ingredient in the dosage form generally is at least 0.1 percent, preferably at least 1 percent, more preferably at least 3 percent, most preferably at least 5 percent and generally up to 70 percent, or up to 50 percent, or up to 30 percent, or up to 25 percent, based on the total weight of the dosage form.

In another aspect of the invention the liquid composition of the present invention may be used for coating dosage forms, such as tablets, granules, pellets, caplets, lozenges, suppositories, pessaries or implantable dosage forms, to form a coated composition. If the liquid composition of the present invention comprises an active ingredient, such as a drug, drug layering can be achieved, i.e., the dosage form and the coating may comprise different active ingredients for different end-uses and/or having different release kinetics.

In yet another aspect of the invention the liquid composition of the present invention may be used for the manufacture of capsules in a process which comprises the step of contacting the liquid composition with dipping pins.

The coated dosage forms and the capsules can be dried or let allowed to dry in a known manner.

The liquid composition and the solid dispersion of the present invention may further comprise optional additives, such as coloring agents, pigments, opacifiers, flavor and taste improvers, antioxidants, plasticizers, surfactants, lubricants, anti-tack agents, glidants, fillers, disintegrants, binders, salts, such as sodium chloride; saccharides, such as white sugar and lactose; a second cellulose ether, and any combination thereof. Optional additives are preferably pharmaceutically acceptable. Useful amounts and types of one or more optional adjuvants are generally known in the art and depend on the intended end-use of the liquid composition or the solid dispersion of the present invention. A large variety of optional adjuvants is disclosed in International Patent Application WO 2005/115330, page 45, line 20-page 46, line 33.

The following examples are for illustrative purposes only and are not intended to limit the scope of the present invention. All percentages are by weight unless otherwise specified.

Example and Comparative Example

Determination of the % Methoxyl and % Hydroxypropoxyl in HPMC

The determination of the % methoxyl and % hydroxypropoxyl in hydroxypropyl methylcellulose (HPMC) was carried out according to the United States Pharmacopeia (USP 35, "Hypromellose", pages 3467-3469).

The values obtained were % methoxyl and % hydroxypropoxyl. These were subsequently converted into degree of substitution (DS) for methoxyl substituents and molar substitution (MS) for hydroxypropoxyl substituents. Residual amounts of salt have been taken into account in the conversion.

Determination of the Viscosity of HPMC

The viscosity of the HPMC samples was measured as a 2.0% by weight solution in water at 20° C.±0.1° C. The 2.0% by weight HPMC solution in water was prepared according to United States Pharmacopeia (USP 35, "Hypromellose", pages 3467-3469), followed by an Ubbelohde viscosity measurement according to DIN 51562-1:1999-01 (January 1999).

Determination of the Ratio Fraction (A)/Fraction (B)

The determination of ether substituents in cellulose ethers is generally known and e.g., described in Carbohydrate Research, 176 (1988) 137-144, Elsevier Science Publishers B.V., Amsterdam, DISTRIBUTION OF SUBSTITUENTS IN O-ETHYL-O-(2-HYDROXYETHYL)CELLULOSE by Bengt Lindberg, Ulf Lindquist, and Olle Stenberg.

Specifically, determination of the ratio fraction (A)/fraction (B) of the unsubstituted hydroxyalkoxyl groups is conducted as follows:

10-12 mg of the hydroxyalkyl methylcellulose, such as hydroxypropyl methylcellulose, are dissolved in 4.0 mL of dry analytical grade dimethyl sulfoxide (DMSO) (Merck, Darmstadt, Germany, stored over 0.3 nm molecular sieve beads) at about 90° C. under stirring and then cooled down to room temperature again. The solution is left stirring at room temperature over night to ensure complete solubilization. The entire reaction including the solubilization of the hydroxyalkyl methylcellulose is performed using a dry nitrogen atmosphere in a 4 mL screw cap vial. After solubilization the dissolved hydroxyalkyl methylcellulose is transferred to a 22 mL screw cap vial. Powdered sodium hydroxide (freshly pestled, analytical grade, Merck, Darmstadt, Germany) and ethyl iodide (for synthesis, stabilized with silver, Merck-Schuchardt, Hohenbrunn, Germany) in a thirty fold molar excess of the reagents sodium hydroxide and ethyl iodide per hydroxyl group of the anhydroglucose unit are added and the solution is vigorously stirred under nitrogen in the dark for three days at ambient temperature. The perethylation is repeated with addition of the threefold amount of the reagents sodium hydroxide and ethyl iodide compared to the first reagent addition and further stirring at room temperature for additional two days. Optionally the reaction mixture can be diluted with up to 1.5 mL DMSO to ensure good mixing during the course of the reaction. 5 mL of 5% aqueous sodium thiosulfate solution is poured into the reaction mixture and the obtained solution is then extracted three times with 4 mL of dichloromethane. The combined extracts are washed three times with 2 mL of water. The organic phase is dried with anhydrous sodium sulfate (ca. 1 g). After filtration the solvent is removed in a gentle stream of nitrogen and the sample is stored at 4° C. until further sample preparation.

Hydrolysis of about 5 mg of the perethylated samples is performed under nitrogen in a 2 mL screw cap vial with 1 mL of 90% aqueous formic acid under stirring at 100° C. for 1 hour. The acid is removed in a stream of nitrogen at 35-40° C. and the hydrolysis is repeated with 1 mL of 2M aqueous trifluoroacetic acid for 3 hours at 120° C. in an inert nitrogen atmosphere under stirring. After completion the acid is removed to dryness in a stream of nitrogen at ambient temperature using ca. 1 mL of toluene for co-distillation.

The residues of the hydrolysis are reduced with 0.5 mL of 0.5 M sodium borodeuteride in 2N aqueous ammonia solution (freshly prepared) for 3 hours at room temperature under stirring. The excess reagent is destroyed by drop wise addition of ca. 200 μL of concentrated acetic acid. The resulting solution is evaporated to dryness in a stream of nitrogen at ca. 35-40° C. and subsequently dried in vacuum for 15 min at room temperature. The viscous residue is dissolved in 0.5 mL of 15% acetic acid in methanol and evaporated to dryness at room temperature. This is done five times and repeated four times with pure methanol. After the final evaporation the sample is dried in vacuum overnight at room temperature.

The residue of the reduction is acetylated with 600 μL of acetic anhydride and 150 μL of pyridine for 3 hrs at 90° C. After cooling the sample vial is filled with toluene and evaporated to dryness in a stream of nitrogen at room temperature. The residue is dissolved in 4 mL of dichloromethane and poured into 2 mL of water and extracted with 2 mL of dichloromethane. The extraction is repeated three times. The combined extracts are washed three times with 4 mL of water and dried with anhydrous sodium sulfate. The dried dichloromethane extract is subsequently submitted to GC analysis. Depending on the sensitivity of the GC system, a further dilution of the extract can be necessary.

Gas-liquid (GLC) chromatographic analyses are performed with Hewlett Packard 5890A and 5890A Series II type of gas chromatographs equipped with J&W capillary columns DB5, 30 m, 0.25 mm ID, 0.25 μm phase layer thickness operated with 1.5 bar helium carrier gas. The gas chromatograph is programmed with a temperature profile that holds constant at 60° C. for 1 min, heats up at a rate of 20° C./min to 200° C., heats further up with a rate of 4° C./min to 250° C., heats further up with a rate of 20° C./min to 310° C. where it is held constant for another 10 min. The injector temperature is set to 280° C. and the temperature of the flame ionization detector (FID) is set to 300° C. 1 μL of the samples is injected in the splitless mode at 0.5 min valve time. Data are acquired and processed with a LabSystems Atlas work station.

Quantitative monomer composition data are obtained from the peak areas measured by GLC with FID detection. Molar responses of the monomers are calculated in line with the effective carbon number (ECN) concept but modified as described in the table below. The effective carbon number (ECN) concept has been described by Ackman (R. G. Ackman, J. Gas Chromatogr., 2 (1964) 173-179 and R. F. Addison, R. G. Ackman, J. Gas Chromatogr., 6 (1968) 135-138) and applied to the quantitative analysis of partially alkylated alditol acetates by Sweet et. al (D. P. Sweet, R. H. Shapiro, P. Albersheim, Carbohyd. Res., 40 (1975) 217-225).

ECN Increments Used for ECN Calculations:

| Type of carbon atom | ECN increment |
|---|---|
| hydrocarbon | 100 |
| primary alcohol | 55 |
| secondary alcohol | 45 |

In order to correct for the different molar responses of the monomers, the peak areas are multiplied by molar response factors MRFmonomer which are defined as the response relative to the 2,3,6-Me monomer. The 2,3,6-Me monomer is chosen as reference since it is present in all samples analyzed in the determination of ratio fraction (A)/fraction (B). MRFmonomer=ECN2,3,6-Me/ECNmonomer The mole fractions of the monomers are calculated by dividing the corrected peak areas by the total corrected peak area.

Based on the mole fractions as defined above the ratio fraction (A)/fraction (B) is determined, wherein fraction (A) represents the sum of all molar fractions of substituted hydroxyalkoxyl groups having hydroxyl groups (of the hydroxyalkoxyl groups) substituted further with methoxyl groups and fraction (B) represents the sum of all molar fractions of unsubstituted hydroxyalkoxyl groups having hydroxyl groups (of the hydroxyalkoxyl groups) not substituted further with methoxyl groups. In Comparative Example A and Example 1 the hydroxyalkoxyl groups are hydroxypropoxyl groups.

Storage Stability

To evaluate the storage stability of a liquid composition of the present invention and of a comparative liquid composition, 10 weight percent of the HPMC of Example 1 and of Comparative Example A each were separately dissolved in a mixture of methanol/water having a weight ratio of 90/10 by stirring at room temperature for 2 hours.

The complex viscosity |η*| of the mixtures comprising the HPMC at 25° C. was investigated in a time sweep experiment using an Anton Paar Physica UDS200 rheometer (Ostfildern, Germany) in oscillation shear flow. A Cup & Bob (Z3-DIN) geometry was used and the upper surface of the geometry was covered with small metal sheets to avoid evaporation. The measurements were performed at a constant frequency of 1 Hz and a constant strain (deformation amplitude) of 0.5% over 18 h in the linear visco-elastic region. These measurements were conducted with a data collection rate of one average value each 5 minutes. The first measurement was conducted 10 minutes after the solution had been prepared as described above. The last measurement was conducted 1080 minutes after preparation of the solution. The results are summarized in Table 1 below. The details of the storage stability measurements are listed in Table 2 below.

Preparation of HPMC Having a Ratio Fraction (A)/Fraction (B) of Less than 0.30, Used for Preparing a Comparative Liquid Composition Hydroxypropyl methylcellulose (HPMC) was produced according to the following procedure. Finely ground wood cellulose pulp was loaded into a jacketed, agitated reactor. The reactor was evacuated and purged with nitrogen to remove oxygen and then evacuated again. A 50 weight percent aqueous solution of sodium hydroxide was sprayed onto the cellulose in an amount of 4.94 moles of sodium hydroxide per mole of anhydroglucose units in the cellulose and the temperature was adjusted to 40° C. After stirring the mixture of aqueous sodium hydroxide solution and cellulose for about 15 minutes at 40° C., 2.79 moles of dimethyl ether and 5.94 moles of methyl chloride per mole of anhydroglucose units were added to the reactor. 2.14 moles of propylene oxide per mole of anhydroglucose units were added to the reactor shortly after the addition of the dimethyl ether and methyl chloride. The contents of the reactor were then heated to 80° C. in 80 min. After having reached 80° C., the reaction was allowed to proceed for 60 min.

After the reaction, the reactor was vented and allowed to cool down. The contents of the reactor were removed and transferred to a tank containing hot water of a temperature of 85-95° C. The crude HPMC was then neutralized with formic acid and washed chloride free with hot water (assessed by $AgNO_3$ flocculation test), cooled to room temperature and dried at 55° C. in an air-swept drier. The material was then ground using an Alpine UPZ mill using a 0.5 mm screen.

The ground HPMC was subsequently partially depolymerized by heating it with about 3 g of gaseous hydrogen chloride per kg of HPMC at 70-80° C. for about 5 hours to achieve a desired viscosity of 3-4 mPa·s. The partially depolymerized HPMC was neutralized with sodium bicarbonate. The produced HPMC had a viscosity of 3.3 mPa·s, measured as 2.0 wt-% solution in water at 20° C.

Preparation of HPMC Having a Ratio Fraction (A)/Fraction (B) of at Least 0.30, Used for Preparing the Liquid Composition of the Present Invention Finely ground wood cellulose pulp was loaded into a jacketed, agitated reactor. The reactor was evacuated and purged with nitrogen to remove oxygen and then evacuated again. The reaction was carried out in two stages. In the first stage a 50 weight percent aqueous solution of sodium hydroxide was sprayed onto the cellulose in an amount of 2.70 moles of sodium hydroxide per mole of anhydroglucose units in the cellulose and the temperature was adjusted to 40° C. After stirring the mixture of aqueous sodium hydroxide solution and cellulose for about 25 minutes at 40° C., 1.02 moles of dimethyl ether and 0.19 moles of methyl chloride per mole of anhydroglucose units were added as a slurry to the reactor. 0.75 moles of propylene oxide per mole of anhydroglucose units were added to the reactor shortly after the addition of the slurry. Stirring was continued for 10 minutes. The contents of the reactor were then heated to 65° C. in 15 min. After having reached 65° C., the first stage reaction was allowed to proceed for 80 min. The contents of the reactor were then cooled to 40° C. within 15 min.

The second stage of the reaction was started by addition of methyl chloride in an amount of 5.14 molar equivalents of methyl chloride per mole of anhydroglucose units. Then a 50 weight percent aqueous solution of sodium hydroxide at an amount of 2.23 moles of sodium hydroxide per mole of anhydroglucose units was added and the temperature was maintained at 40° C. for 5 min. The contents of the reactor were then heated to 82° C. in 80 min. After having reached 82° C., the second stage reaction was allowed to proceed for 30 min.

After the reaction, the reactor was vented and allowed to cool down. The contents of the reactor were removed and transferred to a tank containing hot water of a temperature of 85-95° C. The crude HPMC was then neutralized with formic acid and washed chloride free with hot water (assessed by $AgNO_3$ flocculation test), cooled to room temperature and dried at 55° C. in an air-swept drier. The material was then ground using an Alpine UPZ mill using a 0.5 mm screen.

The ground HPMC was subsequently partially depolymerized by heating it with about 3 g of gaseous hydrogen chloride per kg of HPMC at 80° C. for about 2.5 hours to achieve a desired viscosity of 3-4 mPa·s. The partially depolymerized HPMC was neutralized with sodium bicarbonate. The produced HPMC had a viscosity of 3.6 mPa·s, measured as 2.0 wt-% solution in water at 20° C.

The results in Tables 1 and 2 below illustrate that a liquid composition of the present invention which comprises a HPMC wherein the ratio fraction (A)/fraction (B) is at least 0.30 is much more viscosity-stable upon storage over an extended time period, i.e., a liquid composition of the present invention exhibits a much smaller rate of viscosity increase after storage of the liquid composition over an extended time period, than a liquid composition which comprises a comparable HPMC wherein the ratio fraction (A)/fraction (B) is less than 0.30. The HPMC in the liquid composition of the Example has substantially the same viscosity at 20° C. as 2.0 wt-% solution in water and substantially the same % methoxyl and % hydroxypropoxyl groups as the HPMC in the liquid composition of the Comparative Example, but a significantly higher ratio fraction (A)/fraction (B).

TABLE 1

| Properties of HPMC used in liquid Composition | Comparative Example | Example of the Invention |
|---|---|---|
| HPMC Viscosity as 2.0 wt-% solution in water at 20° C.; mPa · s | 3.3 | 3.6 |
| % methoxyl | 29.5 | 29.5 |
| Calculated DS(methoxyl) | 1.95 | 1.95 |
| % hydroxypropoxyl | 9.9 | 9.5 |
| Calculated MS(hydroxypropoxyl) | 0.27 | 0.26 |
| ratio fraction (A)/fraction (B) | 0.24 | 0.56 |
| complex viscosity \|η *\| of 10 weight percent of HPMC dissolved in a mixture of methanol/water of a weight ratio of 90/10; mPa · s at x min. | | |
| 60 minutes after preparation of solution | 115 | 211 |
| 1080 minutes after preparation of solution | 1480000 | 366 |

TABLE 2

| complex viscosity \|η *\| | 10 weight percent of HPMC dissolved in a mixture of methanol/water of a weight ratio of 90/10 | |
|---|---|---|
| mPa · s at x min. | Comparative Example | Example |
| 10 | 107 | 192 |
| 30 | 91 | 185 |
| 60 | 115 | 211 |
| 120 | 121 | 235 |
| 180 | 143 | 263 |
| 240 | 168 | 270 |
| 300 | 208 | 283 |
| 360 | 242 | 301 |
| 420 | 289 | 305 |
| 480 | 351 | 316 |
| 540 | 5690 | 325 |
| 600 | 505000 | 331 |
| 660 | 1390000 | 339 |
| 720 | 1660000 | 344 |
| 780 | 270000* | 350 |
| 840 | 223000* | 356 |
| 900 | 224000* | 357 |
| 960 | 292000* | 361 |
| 1020 | 689000* | 373 |
| 1080 | 1480000* | 366 |

*Due to gelling of the sample a high error margin is observed in the viscosity measurement

The invention claimed is:

1. A liquid composition comprising a liquid diluent, one or more active ingredients, and at least one hydroxyalkyl methylcellulose wherein hydroxyalkoxyl groups are classified into a fraction (A) and a fraction (B), wherein fraction (A) represents the sum of all molar fractions of substituted hydroxyalkoxyl groups having hydroxyl groups substituted further with methoxyl groups and fraction (B) represents the sum of all molar fractions of unsubstituted hydroxyalkoxyl groups having hydroxyl groups not substituted further with methoxyl groups and wherein the ratio fraction (A)/fraction (B) is from 0.35 to 0.90 and wherein the hydroxyalkyl methylcellulose has a DS of from 1.6 to 2.4 and an MS of from 0.08 to 0.90, wherein DS is the average number of hydroxyl groups substituted by methoxyl groups per anhydroglucose unit and MS is the average number of moles of hydroxyalkoxyl groups per anhydroglucose unit,
   wherein the liquid diluent consists of i) an organic diluent or ii) a blend of more than 50 weight percent of an organic diluent and less than 50 weight percent of water, based on the total weight of the organic diluent and the water, and
   wherein the organic diluent is an alcohol, ether, ketone, acetate or halogenated hydrocarbon.

2. The liquid composition of claim 1 wherein the ratio fraction (A)/fraction (B) in the at least one hydroxyalkyl methylcellulose is from 0.50 to 0.70.

3. The liquid composition of claim 1 wherein the ratio fraction (A)/fraction (B) in the at least one hydroxyalkyl methylcellulose is from 0.50 to 0.65.

4. The liquid composition of claim 1 wherein the at least one hydroxyalkyl methylcellulose has a DS of from 1.7 to 2.2 and an MS of from 0.15 to 0.35.

5. The liquid composition of claim 1 wherein the at least one hydroxyalkyl methylcellulose has a viscosity of from 1.20 to 100 mPa·s, measured as a 2 wt.-% solution in water at 20° C.

6. The liquid composition of claim 1 wherein the at least one hydroxyalkyl methylcellulose is a hydroxypropyl methylcellulose.

7. The liquid composition of claim 1 wherein the at least one hydroxyalkyl methylcellulose has a viscosity of from 1.20 to 50 mPa·s, measured as a 2 wt.-% solution in water at 20° C.

8. The liquid composition of claim 7 wherein the at least one hydroxyalkyl methylcellulose has a viscosity of from 1.8 to 10 mPa·s, measured as a 2 wt.-% solution in water at 20° C.

9. The liquid composition of claim 1 wherein the organic diluent is an alcohol, ether or ketone.

10. The liquid composition of claim 9 wherein the organic diluent is an alcohol or ketone.

11. The liquid composition of claim 1 wherein the viscosity of the liquid composition, measured after 18 hours storage at 25° C., is not more than the 10-fold viscosity of the liquid composition at 25° C. that is measured 60 minutes after the liquid composition has been prepared, when the liquid composition comprises 10 weight percent of the at least one hydroxyalkyl methylcellulose, based on the total weight of the liquid composition.

12. The liquid composition of claim 1 wherein the ratio fraction (A)/fraction (B) in the at least one hydroxyalkyl methylcellulose is from 0.40 to 0.80.

13. The liquid composition of claim 12 wherein the at least one hydroxyalkyl methylcellulose has a viscosity of from 1.20 to 50 mPa·s, measured as a 2 wt.-% solution in water at 20° C.

14. The liquid composition of claim 13 wherein the at least one hydroxyalkyl methylcellulose has a viscosity of from 1.8 to 10 mPa·s, measured as a 2 wt.-% solution in water at 20° C.

15. The liquid composition of claim 14 wherein the at least one hydroxyalkyl methylcellulose is a hydroxypropyl methylcellulose.

16. The liquid composition of claim 15 wherein the at least one hydroxypropyl methylcellulose has a DS of from 1.7 to 2.2 and an MS of from 0.12 to 0.60.

17. The liquid composition of claim 16 wherein the organic diluent is an alcohol, ether or ketone.

18. The liquid composition of claim 17 wherein the organic diluent is an alcohol or ketone.

19. A process for coating a dosage form comprising the step of contacting the liquid composition of claim 1 with the dosage form.

20. A process for the manufacture of capsules comprising the step of contacting the liquid composition of claim 1 with dipping pins.

* * * * *